United States Patent [19]

Howard et al.

[11] 4,235,971

[45] Nov. 25, 1980

[54] INOCULATOR

[75] Inventors: John F. Howard; Felix P. Tolosa; Lawrence Boxer, all of Alexandria, Va.

[73] Assignee: Dynatech Laboratories, Incorporated, Alexandria, Va.

[21] Appl. No.: 914,131

[22] Filed: Jun. 9, 1978

Related U.S. Application Data

[63] Continuation of Ser. No. 680,450, Apr. 26, 1976, abandoned.

[51] Int. Cl.³ .................. C12M 1/32; C12M 1/20; C12M 1/12
[52] U.S. Cl. ............................... 435/293; 435/301; 435/311
[58] Field of Search ........ 195/120, 127, 139, 103.5 M, 195/103.5 K, 103.5 R; 23/230 R, 230 B; 141/237, 238; 422/65, 102; 435/29, 30, 31, 32, 33, 34, 39, 40, 301, 292, 293, 311, 287, 289

[56] References Cited

U.S. PATENT DOCUMENTS

| | | | |
|---|---|---|---|
| 3,356,462 | 12/1967 | Cooke et al. | 23/292 |
| 3,436,171 | 4/1969 | Weichselbaum | 195/120 X |
| 3,455,788 | 7/1969 | Curry et al. | 195/120 X |
| 3,536,449 | 10/1970 | Astle | 23/230 |
| 3,650,360 | 3/1972 | Lancaster | 141/238 |
| 3,728,227 | 4/1973 | Elson et al. | 195/127 |
| 3,772,154 | 11/1973 | Isenberg et al. | 195/127 X |
| 3,912,596 | 10/1975 | Hague et al. | 195/127 |

*Primary Examiner*—Thomas G. Wiseman
*Attorney, Agent, or Firm*—Le Blanc, Nolan, Shur & Nies

[57] ABSTRACT

An inoculator wherein a multiplicity of small volumes of an inoculum are picked up on pins depending from an inoculator head and deposited in separate areas according to a pattern, such as in the wells of a microtitration tray. The instrument includes a control circuit for automatic cycling, and a sterilization furnace is provided that may be included in the operational cycle.

13 Claims, 6 Drawing Figures

INOCULATOR

This is a continuation of application Ser. No. 680,450, filed Apr. 26, 1976, now abandoned.

This invention relates to a partially automated instrument for the simultaneous transfer of small volumes of an inoculum such as a bacterial suspension to an area pattern such as all of the wells of a multi-well test tray or the like, and particularly to related parts and a system for accomplishing the necessary movements of an inoculator head in desired sequence.

In its preferred embodiment the invention will be disclosed for the simultaneous inoculation with an infectious organism of all of the wells of a test tray having a large number of wells, for example ninety-six, each of which wells has been provided with a small volume of a nutrient broth containing in different concentrations an antibiotic hostile to the infectious organism. When the test tray is incubated growth may be detected in wells containing concentrations of antibiotic to which the infectious organism is not susceptible.

A dispensing instrument for charging test trays with the different broth and antibiotic concentrations is disclosed in the pending application of Citrin Ser. No. 595,005 filed July 11, 1975, U.S. Pat. No. 4,093,762; and the instrument of the invention is especially adapted for example to properly inoculate all of the wells of a test tray charged as in the Citrin application in one simple operational cycle.

Another use of the invention is in transferring a multiplicity of small volumes of an inoculum or multiplicity of inocula such as infectious organisms to the surface of a nutrient agar contained in a Petri dish or the like. The agar may contain a known concentration of a specific antibiotic throughout, inhibiting growth of susceptible organisms. Another use is to assay the viability of organisms in each well of a completed test tray, thus differentiating effective antibiotic concentration necessary to inhibit organism growth from concentration necessary to actually kill the organism.

It is therefore the major object of this invention to provide a novel system for the simultaneous inoculation of all of the wells of a multi-well test tray or other areas containing different known concentrations of an antibiotic or the like.

A further object of the invention is to provide a novel instrument wherein an inoculator head carrying a multiplicity of pickup elements such as pins is sequentially driven in a controlled combination of linear movements to pick up a number of small volumes of inoculum from a receptacle and then deposit them simultaneously in the separate wells of a test tray or according to a predetermined area pattern on a nutrient agar surface.

A further object of the invention is to provide a novel instrument wherein an inoculator head is sequentially moved horizontally between inoculum pickup and deposit stations and at each station is imparted controlled vertical movements. In association with this object the instrument may contain a sterilization station having a furnace to which the head may be horizontally moved and vertically reciprocated.

A further object of the invention is to provide a novel instrument wherein an inoculator head is mounted on a vertically reciprocal part that in turn is carried by a support that is horizontally displaceable, and operation in desired sequence is effected through a control system having in circuit separate drive motors for the vertically reciprocable part and the support and having sensing means signalling sequential positions of the head.

Another object of the invention is to provide a novel inoculator having a table on which receptacles containing an inoculum and a material to be inoculated are placed in predetermined spaced relation, and mechanism is provided for sequentially moving an inoculator head to pickup a multiplicity of small quantities of inoculum and deposit them in predetermined pattern in wells or areas of the material to be inoculated.

A further object of the invention is to provide a novel control system for automatic operation of an inoculator head through a cycle.

Further objects will appear in connection with the appended claims and the annexed drawings.

PREFERRED EMBODIMENTS

Figure 1:
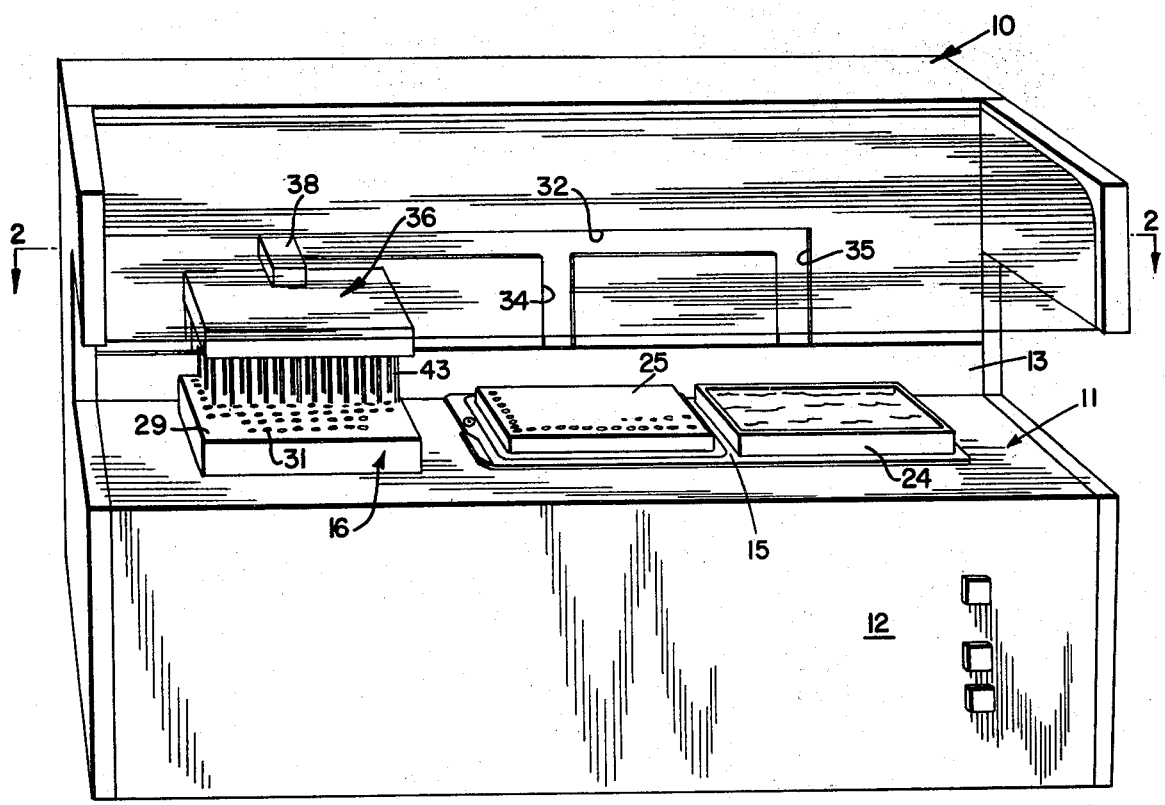
FIG. 1 is a generally perspective front view showing apparatus according to a preferred embodiment.

FIG. 1 shows the complete apparatus enclosed in a sheet metal casing 10 that has a flat horizontal table 11 extending from the top of a vertical front wall 12 to the bottom of a vertical panel 13 that is spaced forwardly from a vertical rear wall (not shown) to provide a mechanism space 14 (FIGS. 2 and 5) housing operating parts to be described.

The top surface of table 11 is preferably smooth, and it mounts a tray holder 15 and a furnace cover 16.

Tray Holder 15 (FIG. 2) is a flat stamped sheet metal element having two longitudinally spaced rectangular opening 17 and 18, and end openings through which extend locating buttons 19 and 20 into threaded sockets in table 11 for locating the tray holder in oriented position on the table. The position of the locating buttons once set, properly locates any alternative design tray holder.

Since the flat tray holder is of thin metal it lies flush on the table surface, and this provides shallow rectangular upwardly open pockets at openings 17 and 18. Two bent up end tabs 22 and 23 provide for lifting the tray holder from the table for removal.

Figure 2:
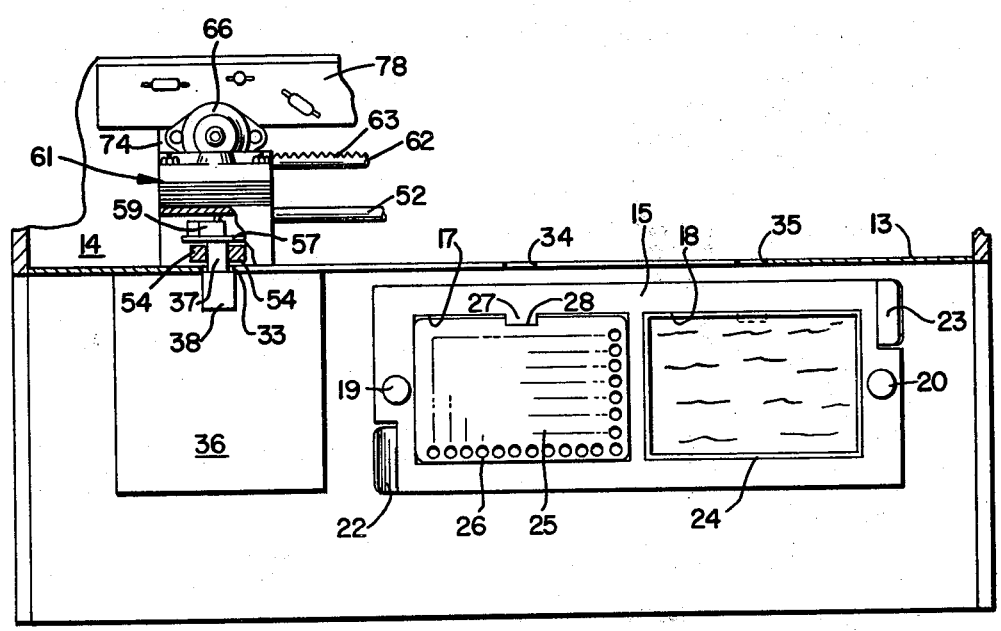
FIG. 2 is a top plan view partly broken away and in section, and looking down in the direction indicated by line 2—2, showing the titration tray holder and some of the mechanism for moving the inoculation head.

In the form shown in FIG. 2, the pockets are each of about the same size and adapted to receive and retain spaced receptacles such as trays 24 and 25. As shown test tray 24 may be an open top reservoir of the inoculum to be transferred, and tray 25 may be a test tray of the microtitration type having a multiplicity of open top wells 26 into each of which a small amount of inoculum is to be deposited simultaneously. At one side of opening 17 a tab 27 extends, and the test tray 25 is formed with a notch 28 adapted to fit with that tab in only one position of the test tray on the table.

Where the material to be inoculated is in a Petri dish of agar the opening 17 may be suited in shape to the dish.

The test tray holder thus serves as a template for accurately locating the positions of the trays 24 and 25 relative to each other and to the furnace 16 which is in fixed location on the table, for a purpose to appear.

Also as shown in FIG. 1, the top wall 29 of the furnace is provided with a multiplicity of small openings 31 having essentially the same arrangement, spacing and orientation as the openings 26 of positioned tray 25.

Vertical panel 13 is formed with a longitudinally extending opening 32, and laterally spaced leg openings 33, 34 and 35 extend vertically downwardly from opening 32. Vertical openings 34 and 35 are dimensional to limit downward travel of the inoculation head 36 to prevent improper initiation of furnace cycle by control circuitry. Furnace cycle is initiated by shutter element 71 carried by a post 37 entering lower sensor 73.

Figure 3:
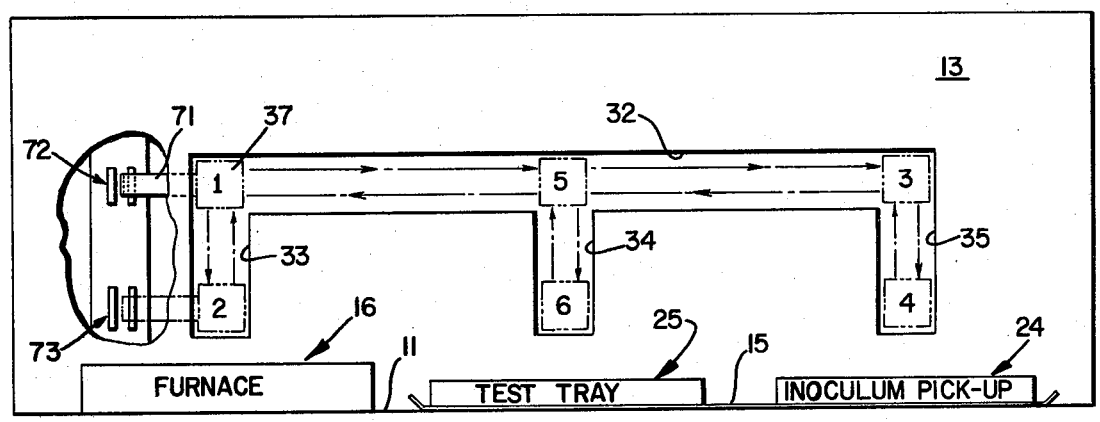
FIG. 3 is a front elevation with the path of the inoculation head mounting post shown diagrammatically.

An inoculation head 36 is mounted upon the post 37 that extends horizontally through these openings 32, 33, 34 and 35 in the various positions of head 36 during operation and has controlled movement along them as diagrammatically indicated in FIG. 3. Post 37 is initially centered longitudinally of the table in opening 32 at the top of depending leg opening 33 and above the furnace 16, at the beginning of each cycle of operations.

Post 37 is preferably of square cross section, and (FIG. 5) a generally U-shaped square-cornered socket 38 secured to the head 36 as by screws 39 fits axially and frictionally tightly on post 37.

At the end of post 37 is an axially adjustable element 41 in the form of a screw threaded into the post, and this element may be adjusted to dispose its flat outer end 42 to define a head locating stop abutted by the bottom of the socket for limiting the inward travel of the head toward panel 13. This adjustment locates the head properly over the furnace as will appear, and the friction mounting coupled with the adjustable stop enables a head to be initially correctly mounted on post 37 and then removed as for cleaning and repair and quickly accurately replaced by even the least skillful operator.

The test tray 25 may be an integral synthetic plastic member having ninety-six upwardly open identical wells in eight straight rows of twelve each. Preferably tray 25 is of the type disclosed in U.S. Pat. No. 3,356,462 to Cooke et al.

Similarly the furnace cover 29 is proved with ninety-six corresponding openings. The longitudinal rows of the tray 25 are aligned with the longitudinal rows of the furnace top, due to the locating action of holder 15.

Figure 5:
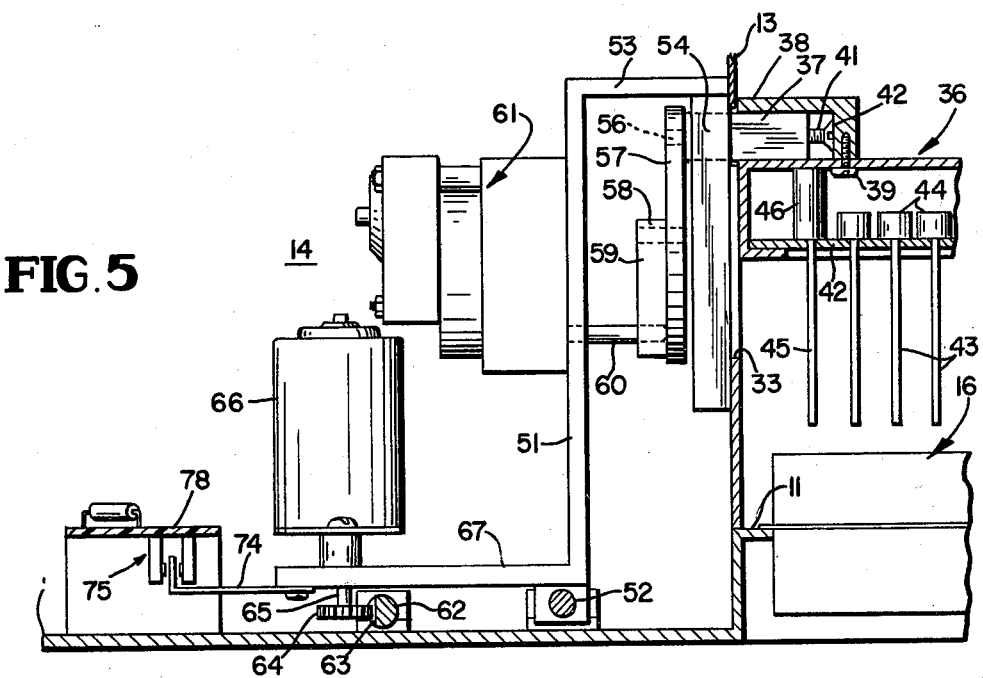
FIG. 5 is an enlarged fragmentary view mainly in section substantially in a vertical plane through the left vertical panel opening in FIG. 3 showing the inoculator head and its drive.

As shown in FIGS. 1 and 5, head 36 carries a multiplicity of depending inoculator pins 43 that are arranged in eight rows of twelve pins each. The adjustable mounting of the head on post 37 insures that initially each pin 43 is aligned with an opening 31 in the furnace cover. The bottom wall 42 of the box-like head is removable and serves as a pin locating plate, with each pin 43 extending slidably through an aperture in that plate and terminating in an enlarged upper end 44.

A marking pin 45 may also be carried by the head for certain purposes as will appear, and it extends from an enlarged upper end 46 slidably through plate 42. As shown it will be noted that pins 43 are essentially axially loosely supported in the head, while the marking pin when used extends to solidly contact the upper wall.

By making the plate 42 removable any number and arrangement of inoculator pins 43 within the ninety-six opening pattern may be readily provided for different test pattern operations.

Within space 14 a support structure 51 is slidably mounted as on a rod 52 for travel parallel to the table 11 longitudinally of the table. An upper leg 53 of the support carries a depending guide structure providing side guides 54 slidably embracing the parallel sides of post 37 whereby post 37 may be guided for vertical reciprocation.

At its inner end post 37 is pivotally mounted on a horizontal axis at 56 on a cam or link member 57 that in turn is pivotally connected at 58 to an eccentric 59 driven by the output shaft 60 of an electric motor 61 on support 51. When motor unit 61 is actuated, post 37 is thereby caused to reciprocate vertically in guides 54.

Extending parallel to rod 52 is a stationary rack bar 62 having teeth 63 meshed with a gear 64 on the output shaft 65 of a second electric motor 66 that is mounted on a lower support arm 67. When motor 66 is actuated, support 53 is caused to move horizontally longitudinally of table 11 and inoculation head 36 is caused to move in a horizontal path above the top surface of the table.

FIG. 3 diagrammatically shows a cycle of operation for a typical test operation.

Initially post 37 is located at the left end of opening 32 and above opening 33. This locates the head 36 above the furnace with the pins 43 aligned with furnace openings 31. This alignment can be assured by adjustment of screw 41. A test tray 25 with the wells 26 containing material to be inoculated and a receptacle 24 containing the inoculum are mounted on the table in holder 15.

The furnace may be of the type employing quartz heater units, so that its activation may be accomplished by simple switching.

Motor unit 61 is initially activated to reciprocate post 37 between positions 1 and 2 in FIG. 3. Due to the eccentric cam linkage at 59, 57 one revolution of eccentric 59 effects descent of post 37 until at the bottom of the stroke the linkage reverses to effect ascent to a position in opening 32. In this operation post 37 moves down opening 33 until the lower tips of pins 43 are within the furnace for a sterilization period and then moved back up to position 1 at which time motor unit 61 is deactivated.

Now motor 66 is activated and post 37 is moved along opening 32 to shift head 36 longitudinally of table 11 to position 3 above and aligned with the inoculum pickup receptacle 24. At this point motor 66 is disabled and motor unit 61 is again actuated to reciprocate post 37 between position 3 and 4 to move head 36 down until the tips of pins 43 are all immersed in the inoculum and then back up to position 3 where the motor unit 61 is deactivated.

At this point motor 66 is again actuated but in reverse to move post 37 along opening 32 to position 5 where motor 66 is deactivated. At this time the head 36 has been horizontally displaced until pins 43 are aligned with respective wells 26 in test tray 25.

Now motor unit 61 is actuated to vertically reciprocate post 37 in opening 34 between positions 5 and 6, there being a short dwell at position 6 for ensuring transfer of the inoculum.

At this point motor 66 is reactivated to return post 37 along opening 32 to position 1 where motor 66 is deactivated.

The cycle may terminate with motor unit 6 being once more activated to reciprocate the head between positions 1 and 2 for repeating the sterilization operation and then restoring the head to the initial location of position 1.

The gear reduction at motor unit 61 provides for relatively slow vertical reciprocation of the head, as compared with the faster longitudinal travel of the head. This is important in providing for adequately long pickup, inoculation and sterilization periods.

Figure 4:
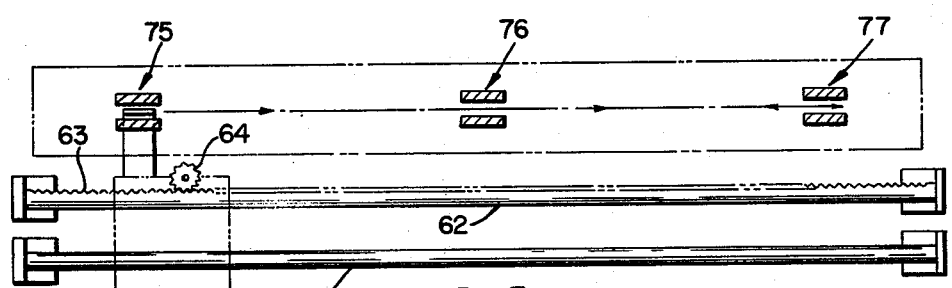
FIG. 4 is a fragmentary view showing detail.

Referring again to FIG. 3, a shutter element 71 is shown as mounted on post 37, adapted to enter between upper and lower pairs of sensors 72 and 73 in the two vertical limit positions of head 36. Actually post 37 itself may serve as the shutter passing between upper and lower pairs of sensors carried by guides 54. In FIGS. 4 and 5 is shown a shutter element 74 carried by support 51 and adapted to enter between pairs of sensors 75, 76 and 77 carried by a printed circuit board 78 and disposed in the longitudinal operative positions of the post 37.

Figure 6:
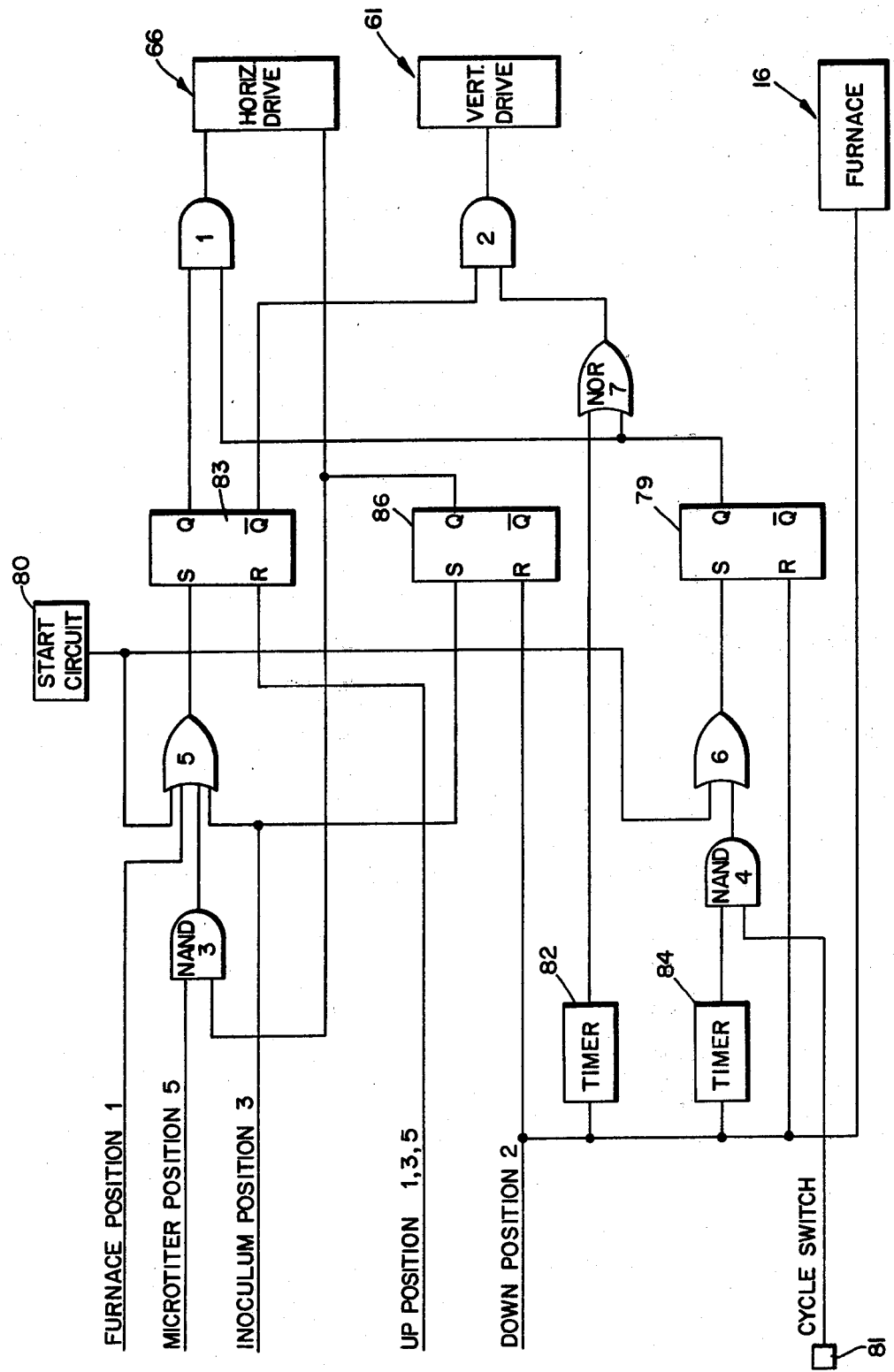
FIG. 6 is a diagrammatic representation of a circuit for explaining operation.

Board 78 may also mount a logic circuit for operation and control which is schematically illustrated in FIG. 6 and will now be described in association with operation of the device.

INOCULATOR LOGIC

The inoculator control system determines the proper sequencing of the inoculator functions. The board 78 takes six inputs including the three horizontal position sensors 75, 76, 77 for the three longitudinal stopping or dwell stations on the inoculator, the two vertical position sensors 72, 73 for the upper and lower limits of the inoculating head vertical travel and a cycle switch 81. The logic essentially controls three functions, a vertical drive, a horizontal drive and a furnace.

When the inoculator power is turned on as at switch 80 the Start Circuit turns on the drive power and selects the vertical drive, and the inoculating head 36 lowers to dip the pin ends into the furnace. When the head reaches its lowest position the down position signal derived from sensor 73 shuts off the drive power, sets the direction select to right and activates two timers, a sterilizer timer 82 for controlling the furnace and a cooling timer 84 for controlling a pin cooling fan (not shown). The down position signal also activates the furnace to sterilize the pins on the inoculating head. After a delay of about 20 seconds the sterilizer timer 82 reapplies power to the vertical drive 61 through NOR-7. The down position signal thus disappears and this deactivates the furnace as the head 36 travels upward to its topmost position at 1 in FIG. 3 and the up position signal from sensor 72 changes the drive select 83 to the horizontal drive. The horizontal drive does not yet function because the drive power is not applied to it. The cool timer causes the fan to cool the sterilized pins 43 for a short period. This unit is usually inoperable for about 25 seconds while the head cools down. The cool timer 84 then enables the cycle switch through NAND-4 and lights an indicator lamp (not shown) on the cycle switch. The inoculator is now conditioned for an automatic cycle.

To start the inoculator in automatic operation, the cycle switch 81 is depressed activating the drive power at 79. The drive select 83 has already been set to the horizontal drive and the inoculating head therefore travels to the right along opening 32 in FIGS. 1 and 3. As the head arrives at position 5 in FIG. 3 a signal is generated at sensor 76 but it is disabled at NAND-3 and the head 36 continues to travel to the right. When the inoculum pickup position 6 of FIG. 3 is reached, an inoculum position signal from sensor 77 changes the drive select 83 to vertical drive and resets the direction select 86 to left. The head now lowers to dip pins 43 into the inoculum and then reverses direction until it is raised to its uppermost position at 3 in FIG. 3. The up position signal from sensor 77 now changes the drive select 83 to the horizontal drive. Because the direction select 86 has already been set to left, the inoculating head now travels back to the left along opening 32. When the head reaches position 5 in FIG. 3 a signal is generated at sensor 76, and since the direction select 86 has enabled NAND-3 that signal passes through to the drive select 83 changing it to vertical drive. The head now lowers to dip the pin ends into the tray wells and reverses direction to travel upward until the topmost position at 5 is reached and an up position signal is generated. This changes the drive select 83 to horizontal drive and the head continues to travel left.

When the head reaches the furnace position 1 of FIG. 3 a furnace position signal from sensor 75 changes the drive select 83 to vertical drive and the head lowers into the furnace. From this point until the cycle switch can be activated again, the logic operation is the same as described for the start-up sterilization.

It will be noted that a signal from sensor 73 may not be used at the down positions 4 and 6 in FIG. 3. That is because merely dipping the ends of the pins into the inoculum and the tray wells respectively is sufficient for the operative pickup and inoculation steps. Also in some instances there need be no sterilization whereby the lower sensor 73 has no function.

The sensors 72–77 may be of any type, as for example photocell-light beams combinations or capacitance switches.

Any equivalent electrical or mechanical control for accomplishing the foregoing sequential movements of head 36 is within the scope of the invention.

The invention may be embodied in other specific forms without departing from the spirit or essential characteristics thereof. The present embodiments are therefore to be considered in all respects as illustrative and not restrictive the scope of the invention being indicated by the appended claims rather than by the foregoing description, and all changes which come within the meaning and range of equivalency of the claims are therefore intended to be embraced therein.

What is claimed and desired to be secured by Letters Patent is:

1. An automated inoculator apparatus for the simultaneous transfer of small volumes of material in a predetermined pattern, comprising a support, means providing a stationary reservoir station on said support, means providing a stationary deposit station for mounting a receptacle on said support alongside but in spaced relation to said reservoir, means defining a stationary sterilizing furnace station on said support at the opposite side of the deposit station from said reservoir, an inoculation head having a multiplicity of downwardly projecting material pickup elements arranged in a predetermined pattern movably mounted on said support and initially disposed in a position above said sterilization station, means for displacing said head from said initial position along a substantially horizontal path on said support to dwell positions above said reservoir and deposit stations in sequence and then back to said initial position, means for vertically reciprocating said head when it is in a dwell position above said reservoir to lower said head to cause said pickup elements to pickup small volumes of said material from the reservoir and then raise the head back to said path, means for vertically reciprocating said head when it is in a dwell position above said deposit station to lower said head to cause said pickup elements to deposit material in said pattern in said receptacle at said deposit station and then raise the head back to said path, means effective when said head has returned to said initial position in said path for reciprocating the head vertically to first lower said head to simultaneously dispose all of said pickup elements in the furnace for a sterilization period and then raise said head back to said initial position in said path, and a control system operably connected for cyclically, automatically effecting said head movements in predetermined sequence.

2. Inoculator apparatus as defined in claim 1, further comprising means for effecting movement of said head along said horizontal path at a higher rate of speed than during vertical reciprocation.

3. The apparatus defined in claim 1, wherein said receptacle is a tray that has the same number of test cells arranged in the same pattern as the number and pattern of pickup elements on the head, whereby upon lowering of said head at the deposit station each said test cell simultaneously receives liquid from an associated pickup element.

4. The apparatus defined in claim 1, said control system including separate motors for effecting horizontal and vertical movements of said head and a control circuit for said motors containing sensing means responsive to the position of said head for determining the sequence of head movements.

5. Inoculator apparatus comprising support means including a generally horizontal surface, and a portion located above and to one side of said horizontal surface, stationary receptacle holder means mounted on said surface for locating in side by side spaced relation on said surface a first receptacle containing inoculum and a separate second receptacle for deposit of said inoculum in a predetermined area pattern, a stationary furnace mounted on said surface at the side of said second receptacle opposite the first receptacle into which said pickup elements may be thrust for sterilization, an inoculator head movably mounted on said support means portion and initially disposed in a position above said furnace, means on said support means portion for driving said head along a horizontal path from said initial position in timed sequence to a first dwell position above said first receptacle, a second dwell position above said second receptacle and then back to said initial position, means for vertically reciprocating said head down and then up back to said path when it is at each of said dwell positions above the receptacles, said head having a multiplicity of depending inoculum pickup elements arranged in said pattern whereby small quantities of inoculum from said first receptacle may be simultaneously transferred in said pattern from said first receptacle to said second receptacle, and means operable when the head is returned to said initial position in said path for lowering said pickup elements into said furnace for a sterilization period wherein all of said elements are sterilized simultaneously and then returning the head to said initial position.

6. The apparatus defined in claim 1, wherein said depending pickup elements are pins and said second receptacle is a multi-well tray having wells corresponding in number and pattern to the pins.

7. The apparatus defined in claim 6, wherein said receptacle holder means comprises a template for permitting mounting of said tray only in a predetermined orientation.

8. The apparatus defined in claim 1, wherein said holder means is a thin plate-like member detatchably secured to said surface and having accurately spaced openings therein for seating both of said receptacles.

9. The apparatus defined in claim 1, wherein said head is mounted on a vertically slidable post on a carriage that is horizontally movable on said support means portion, and the means for vertically reciprocating said head comprises a motor on said carriage and linkage connecting said motor to said post.

10. The apparatus defined in claim 9, wherein said means for driving said carriage is a motor unit on the carriage having an output gear meshed with a rack bar on said support means portion.

11. The apparatus defined in claim 1, wherein said head is carried by a post that extends horizontally over said surface, and adjustment means is provided whereby said head may be positioned on said post to align said pickup elements with said deposit areas.

12. The apparatus defined in claim 11, wherein said head has a slidable socket connection and there is an adjustable abutment on said post cooperating with said socket for determining the position of the head on the post.

13. The apparatus defined in claim 1, wherein said furnace has a top cover provided with openings according to said pattern.

* * * * *